(12) United States Patent
Tobita

(10) Patent No.: US 7,867,961 B2
(45) Date of Patent: Jan. 11, 2011

(54) WASH COMPOSITION

(75) Inventor: Kazuhiko Tobita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 567 days.

(21) Appl. No.: 11/685,421

(22) Filed: Mar. 13, 2007

(65) Prior Publication Data

US 2007/0213244 A1 Sep. 13, 2007

Related U.S. Application Data

(63) Continuation of application No. PCT/JP2005/001710, filed on Sep. 9, 2005.

(30) Foreign Application Priority Data

Sep. 13, 2004 (JP) ............................. 2004-264792

(51) Int. Cl.
*C11D 1/02* (2006.01)
*C11D 3/20* (2006.01)
*C11D 3/26* (2006.01)
*C11D 3/33* (2006.01)

(52) U.S. Cl. ................... 510/126; 510/130; 510/136; 510/137; 510/138; 510/467; 510/488; 510/501; 510/505

(58) Field of Classification Search .................. 510/126, 510/130, 136, 137, 138, 467, 488, 501, 505
See application file for complete search history.

(56) References Cited

U.S. PATENT DOCUMENTS

| | | | | |
|---|---|---|---|---|
| 3,707,505 | A | * | 12/1972 | Maeda ...................... 510/392 |
| 5,190,747 | A | * | 3/1993 | Sekiguchi et al. ............. 424/56 |
| 5,328,630 | A | * | 7/1994 | Nozaki et al. ................ 510/427 |
| 5,417,875 | A | * | 5/1995 | Nozaki ....................... 510/386 |
| 5,529,712 | A | * | 6/1996 | Sano et al. ................... 510/481 |
| 5,616,552 | A | * | 4/1997 | Yoshihara et al. ............. 510/490 |
| 6,248,338 | B1 | | 6/2001 | Müller et al. |
| 6,903,057 | B1 | | 6/2005 | Tsaur |
| 2004/0198630 | A1 | * | 10/2004 | Schmid et al. ............... 510/499 |
| 2007/0037728 | A1 | | 2/2007 | Kunieda et al. |

FOREIGN PATENT DOCUMENTS

| | | |
|---|---|---|
| EP | 0 912 164 A1 | 5/1999 |
| EP | 1 496 853 A1 | 1/2005 |
| JP | 5-156288 | 6/1993 |
| JP | 5-156299 | 6/1993 |
| JP | 7-331282 | 12/1995 |
| JP | 8-60189 | 3/1996 |
| JP | 8-134494 | 5/1996 |
| JP | 9-157140 | 6/1997 |
| JP | 2000-514435 | 10/2000 |
| JP | 2001-122742 | 5/2001 |
| JP | 2005-530718 | 10/2005 |
| WO | WO 98/01109 | 1/1998 |
| WO | WO03/022966 | * 3/2003 |
| WO | WO 03/084500 A1 | 10/2003 |
| WO | WO 2005/110356 A1 | 11/2005 |

OTHER PUBLICATIONS

Haruhiko Okuyama, et al., "Senzai Senjo no Jiten", Nov. 25, 1990, p. 572.
U.S. Appl. No. 11/770,113, filed Jun. 28, 2007, Tobita.
International Cosmetic Ingredient Dictionary and Handbook, vol. 2, Ninth Edition, pp. 1563-1564, 2002.
Technical Bulletin, "PURE-GEL® Starches of Personal Care Applications", 2 pgs., (2003).
Certified Priority Document for International Application No. PCT/EP05/005128, Nov. 2005.
Haruhiko Okuyama, et al., "Skin Cleanser and Composition", Motoi Ed., Dictionary for Detergents and Washing, Asakura Publishing Co., Ltd., Nov. 25, 1990, pp. 271-572 (English Translation).

* cited by examiner

*Primary Examiner*—Gregory R Del Cotto
(74) *Attorney, Agent, or Firm*—Oblon, Spivak, McClelland, Maier & Neustadt, L.L.P.

(57) ABSTRACT

To provide a wash composition comprising an N-long-chain-acyl amino acid and/or its salt, especially an N-long-chain-acyl neutral amino acid and/or its salt and hydroxypropyl starch phosphate and excellent in foam properties, washing power and feeling upon use, and to provide cosmetics containing the same. A wash composition comprises (A) an N-long-chain-acyl amino acid and/or its salt, especially an N-long-chain-acyl neutral amino acid and/or its salt and (B) hydroxypropyl starch phosphate. Further, it comprises (C) a fatty acid to improve foaming speed, and (D) an acyl acidic amino acid ester to improve moist feeling after drying.

14 Claims, No Drawings

WASH COMPOSITION

TECHNICAL FIELD

The present invention relates to a wash composition containing an N-lonq-chain-acyl amino acid and/or its salt More particularly, the present invention relates to a wash composition containing an N-long-chain-acylneutral aminoacid and/or its salt and hydroxypropyl starch phosphate. The wash composition of the present invention exhibits low skin and hair irritation has excellent foaming properties (e.g., foaming power and foam retention power), pleasurable feeling upon use, and has excellent washing power for makeup and sebum.

More specifically, the present invention relates to a wash composition in which an N-long-chain-acyl amino acid and/or its salt is an N-long-chain-acyl neutral amino acid and/or its salt. The wash composition of the present invention may further contain a fatty acid, and/or an acyl acidic amino acid ester. The present invention further relates to cosmetics containing the wash composition.

BACKGROUND ART

Skin or hair wash compositions are generally made mainly of an anionic surfactant such as an alkyl sulfate or an alkyl sulfonate. These have been excellent in washing power, but problematic in irritation.

Meanwhile, an N-long-chain-acyl amino acid and/or its salt has been known to be useful as a less irritant material. However, this material has not been unsatisfactory at a practical level in some types of amino acids, especially in neutral amino acids in the aspect of foaming or washing power.

In order to improve the foam properties of N-long-chain-acyl neutral amino acid salts for solving this problem, there are an example of mixing an N-long-chain-acyl neutral amino acid salt with a cationic polymer (Patent Document 1: gazette of JP-A-5-156299) and an example of mixing an acyl glycine salt with a chelating agent and a water-soluble high-molecular compound (Patent Document 2: gazette of JP-A-7-331282). These examples have been improved in foam properties of an N-long-chain-acyl neutral amino acid salt, but poor in washing power. Further, there is an example of mixing an N-long-chain-acyl neutral amino acid salt with a nonionic surfactant having a specific structure of HLB of at least 3 but less than 8 for improving washing property of an N-long-chain-acyl neutral amino acid-containing wash (Patent Document 3: gazette of JP-A-5-156288). Although the incorporation of the nonionic surfactant improved the washing function, satisfactory foam properties were not necessarily obtained.

Accordingly, a wash composition using an N-long-chain-acyl amino acid and/or its salt, especially an N-long-chain-acyl neutral amino acid and/or its salt which less irritate(s) the skin or the hair, satisfying both of the high foam properties and the high washing power and having the excellent feeling upon use has been in high demand.

[Patent Document 1] gazette of JP-A-5-156299
[Patent Document 2] gazette of JP-A-7-331282
[Patent Document 3] gazette of JP-A-5-156283

DISCLOSURE OF THE INVENTION

An object of the invention is to provide a wash composition comprising an N-long-chain-acyl amino acid and/or its salt, especially, an N-long-chain-acyl neutral amino acid and/or its salt and satisfying both of excellent foam properties and washing power, and further to provide washes and cosmetics comprising the same and maintaining excellent feeling upon use.

The present inventors have assiduously conducted investigations to solve the foregoing problems, and have consequently found that a wash composition comprising an N-long-chain-acyl amino acid and/or its salt, especially an N-long-chain-acyl neutral amino acid and/or its salt and hydroxypropyl starch phosphate attains the foregoing object. This finding has led to the completion of the invention.

That is, the invention includes the following embodiments.
[1] A wash composition comprising (A) an N-long-chain-acyl amino acid and/or its salt, and (B) hydroxypropyl starch phosphate.
[2] The wash composition according to [1], wherein (A) the N-long-chain-acyl amino acid and/or its salt are/is an N-long-chain-acyl neutral amino acid and/or its salt.
[3] The wash composition according to any of [1] and [2] which further comprises (C) a fatty acid.
[4] The wash composition according to any one of [1] to [3] which further comprises (D) an acyl acidic amino acid ester.
[5] The wash composition according to any one of [1] to [4], wherein the amino acid of component (A) is glycine.
[6] The wash composition according to any one of [1] to [4], wherein the amino acid of component (A) is alanine.
[7] The wash composition according to any one of [1] to [6], wherein a component (A) to component (B) weight ratio is from 99:1 to 70:30.
[8] A cosmetic containing the wash composition according to any one of [1] to [7].

Excellent washing power and foam properties can be provided by mixing an N-long-chain-acyl amino acid and/or its salt, especially an N-long-chain-acyl neutral amino acid and/or its salt with hydroxypropyl starch phosphate. Washes or cosmetics of the skin, the hair or the like which comprise an N-long-chain-acyl amino acid and/or its salt, especially an N-long-chain-acyl neutral amino acid and/or its salt and which are good in feeling upon use while keeping washing power and foaming properties can be provided by this wash composition.

BEST MODE FOR CARRYING OUT THE INVENTION

The N-long-chain-acyl amino acid and/or its salt, especially the N-long-chain-acyl neutral amino acid and/or its salt as component (A) used in the invention may be obtained by a known method. For example, a Schotten-Baumann reaction of an amino acid and a fatty acid halide is a widely known method.

As the amino acid of component (A), acidic amino acids such as glutamic acid and aspartic acid, neutral amino acids such as glycine, alanine and threonine and basic amino acids such as arginine, lysine and ornithine are available. These amino acids may be T-isomers, D-isomers, DL-isomers or mixtures of two or more selected therefrom. From the standpoint of good stability and good feeling upon use of the material after acylation, acidic amino acids and neutral amino acids are preferable, and neutral amino acids are more preferable. Of acidic amino acids, glutamic acid is preferable. Of neutral amino acids, glycine and alanine are preferable.

As the acyl group of component (A), linear or branched acyl groups derived from saturated or unsaturated fatty acids having from 8 to 22 carbon atoms are available. Thus, in the context of the present invention, the term "long-chain-acyl" is understood to mean a linear or branched, saturated or unsaturated, fatty acid having from 8 to 22 carbon atoms. Examples of the fatty acids include caprylic acid, capric acid, lauric acid, myristic acid, stearic acid, isostearic acid, palmitic acid, oleic acid, linoleic acid, behenic acid, coconut oil fatty acid, palm fatty acid, hardened tallow fatty acid and the like. They may be used either singly or in admixture of two or more selected from the foregoing groups. Especially in view of good foaming and good foam quality, coconut oil fatty acid lauric acid and myristic acid are preferable.

The salt of component (A) is not particularly limited. Examples thereof include inorganic salts for example, alkali metals such as sodium and potassium, alkaline earth metals such as calcium and magnesium, aluminum and zinc, and organic salts, for example, ammonia, organic amines such as monoethanolamine, diethanolamine and triethanolamine, and basic amino acids such as arginine and lysine. They may be used either singly or in admixture of two or more selected from the foregoing groups. In view of easy procurement and handleability, alkali metal salts, organic amine salts and basic amino acids are preferable, and sodium potassium, triethanolamine and arginine are especially preferable.

As hydroxypropyl starch phosphate (CAS No 113894-92-1) as component (B) used in the invention, for example, commercially available STRUCTURE XL (manufactured by National Starch) can be used.

With respect to the fatty acid as component (C) used in the invention, linear or branched compounds derived from saturated or unsaturated fatty acids having from 8 to 22 carbon atoms are available. Examples of the fatty acids include caprylic acid, capric acid, lauric acid, myristic acid, stearic acid, isostearic acid, palmitic acid, oleic acid, linoleic acid, behenic acid, coconut oil fatty acid, palm fatty acid, hardened tallow fatty acid and the like. They may be used either singly or in admixture of two or more selected from the foregoing groups. Especially in view of excellent foaming speed good foaming and good foam quality coconut oil fatty acid, lauric acid and myristic acid are preferable.

Examples of the acyl acidic amino acid ester as component (D) used in the invention Include commercially available "Eldew" CL-301 (di(cholesteryl/behenyl/octyldodecyl) N-lauroyl-L-alutamate (manufactured by Ajinomoto Co., Inc.), "Eldew" CL-202 (di(cholesteryl/octyldodecyl) N-lauroyl-L-qlutamate manufactured by Ajinomoto Co., Inc.), "Eldew" PS-203 (di(phytosteryl/octyldodecyl) N-lauroyl-L-glutamate manufactured by A inomoto Co., Inc.), "Eldew" PS-304 (di(phytosteryl/behenyl/octyldodecyl) N-lauroyl-L-glutamate manufactured by Ajinomoto Co., Inc.), and the like. Especially in view of persistence of feeling upon use and moist feeling, di(phytosteryl/behenyl/octyldodecyl) N-lauroyl-L-qlutamate, di(cholesteryl/behenyl/octyldodecyl) N-lauroyl-L-glutamate and di(phytosteryl/octyldodecyl) N-lauroyl-L-glutamate are preferable A component (A) to component (B) weight ratio used in the invention is usually from 99:1 to 70:30. There are problems that when component (B) is less than 1 foam retention power and washing power are weak, and when component (B) is more than 30, an amount of foams is decreased. For providing both of the excellent washing power and foam properties, the component (A) to component (B) ratio is preferably from 97:3 to 75:25, more preferably from 95:5 to 80:20.

A component A) to component (C) weight ratio used in the invention is usually from 99-1 to 50:50. There are problems that when component (C) is less than 0.1 better washing power is not obtained, and when component (C) is more than 50, feeling upon use inherent in component (A) is impaired. For imparting excellent foam properties) the component (A) to component (C) ratio is preferably from 95:5 to 70-30, more preferably from 90:10 to 80:20.

A component (A) to component (D) weight ratio used in the invention is usually from 99.9:0.1 to 70:30. There are problems that when component (D) is less than 0.1, better washing power is not obtained, and when component (D) is more than 30, foam properties are impaired. For imparting excellent washing power and foam properties, the component (A) to component (D) ratio is preferably from 99.5:0.5 to 75:25, more preferably from 99:1 to 80:20.

The total amount of component (A) varies with the form of the wash composition. It is preferably from 3 to 50% by weight in a liquid wash, from 10 to 70% by weight in a paste wash, from 40 to 95% by weight in a solid wash and from 5 to 70% by weight in a wash powder.

The wash composition of the invention can properly contain, other than the foregoing essential components, various arbitrary components used in ordinary cosmetics, quasi-drugs and the like unless impairing the effects of the invention. Specifically, it is possible to incorporate oils, surfactants, thickeners, antiseptics, aromas, ultraviolet absorbers, humectants, physiologically active ingredients, antioxidants, antiinflammatory agents, antibacterial agents, antiperspirants, chelating agents, neutralizers, pH adjustors and the likes and these can be incorporated according to the specific use and form of washes and cosmetics.

The wash composition of the invention is produced by an ordinary method, and can take the form of a liquid, a paste, a gel, a powder, a solid or the like. It is appropriate as cosmetics of the skin, the hair and the like.

The use of the wash composition of the invention is not particularly limited, but various cosmetics can be provided. Examples thereof include cleaning products such as toilet soaps, face washes (including cream paste, liquid gel, aerosol and the like), shampoos, makeup removers and cleansings, basic products such as hair treatments (including creamy products, misty products, oil products, gel products, products of other forms, and split hair coating agents) and shaving creams (after-shaving creams, shaving creams and the like), and so forth. Application to cleaning products and hair care products is preferable in view of excellent washing power, foam properties and feeling upon use

EXAMPLES

The invention is illustrated specifically below by referring to Examples. However, the invention is not limited by the following Examples.

Example 1 to Example 3

Wash compositions according to formulations shown in Table 1 below were prepared, and these wash compositions were subjected to evaluation of washing the skin and the skin with makeup by five expert panelists. An amount of foams foam retention power, washing power, feelings upon use (foaming speed, rinsing speed, fresh feeling after rinsing and moist feeling after drying) were evaluated according to the following methods and scores Average values of evaluation scores by five panelists were calculated. A score of at least 1 and less than 2 was defined as x; a score of at least 2 and less than 3 as Δ; a score of at least 3 and less than 4 as ○; and a score of at least 4 and at most 5 as ○○. The results are shown in Table 1 below.

(Evaluation of the Amount of Foams)
Score
    5: very large
    4: slightly large
    3: common
    2: slightly small
    1: small (Evaluation of Foam Retention Power)
Score
    5: very high foam retention power
    4: slightly high foam retention power
    3: common
    2: slightly low foam retention power
    1: no foam retention power (Evaluation of Washing Power)
Score
    5: Makeup is removed.
    4: Makeup is slightly removed.
    3: common
    2: Makeup is less removed.
    1: Makeup is not removed.

(Evaluation of Foaming Speed)
Score
    5: very quick
    4: slightly quick
    3: common
    2: slightly slow
    1: slow (Evaluation of Rinsing Speed)
Score
    5: very quick
    4: slightly quick
    3: common
    2: slightly slow
    2: slow (Evaluation of Fresh Feeling After Rinsing)
Score
    5: very good
    4: good
    3: fair
    2: slightly bad
    1: bad (Evaluation of Moist Feeling After Drying)
Score
    5: very good
    4: good
    3: fair
    2: slightly bad
    1: bad

TABLE 1

|  | Example 1 | Example 2 | Example 3 | Comparative Example 1 | Comparative Example 2 | Comparative Example 3 |
| --- | --- | --- | --- | --- | --- | --- |
| Sodium cocoyl glycinate | 30 | 30 | 30 | 30 | 30 | 30 |
| Hydroxypropyl starch phosphate | 2 | 2 | 2 | — | — | — |
| Lauric acid | — | 2 | 2 | — | — | — |
| Myristic acid | — | 2 | 2 | — | — | — |
| Di(phytosteryl/octyldodecyl)N-lauroyl-L-glutamate | — | — | 0.5 | — | — | — |
| Marcoat 550 | — | — | — | 2 | — | — |
| Hydroxypropyl cellulose | — | — | — | — | 2 | — |
| Polyoxyethylene(10)polyoxypropylene(7)butyl ether | — | — | — | — | — | 10 |
| Water | balance | balance | balance | balance | balance | balance |
|  | 100 | 100 | 100 | 100 | 100 | 100 |
| Amount of foams | ⊚ | ⊚ | ⊚ | Δ | ○ | x |
| Foam retention power | ⊚ | ⊚ | ⊚ | ○ | Δ | ○ |
| Washing power | ⊚ | ⊚ | ⊚ | x | x | ○ |
| Foaming speed | ○ | ⊚ | ⊚ | x | Δ | x |
| Rinsing speed | ⊚ | ⊚ | ⊚ | Δ | Δ | x |
| Fresh feeling after rinsing | ⊚ | ⊚ | ⊚ | Δ | Δ | x |
| Moist feeling after drying | ○ | ○ | ⊚ | ○ | Δ | ○ |

As is apparent from the results of Table 1, it has been found that the wash composition comprising the N-long-chain-acyl neutral amino acid and/or its salt as component (A) and hydroxypropyl starch phosphate as component (B) is excellent in foam properties, washing power and feeling upon use It has been further found that the fatty acid as component (C) is incorporated to improve the foaming speed and the acyl acidic amino acid ester as component (D) is incorporated to be able to impart the moist feeling after washing.

Formulation Examples 1 to 4

A face wash foam (Formulation Example 1), a face wash powder formulation Example 2), a liquid face wash (Formulation Example 3) and a face wash foam (Formulation Example 4) obtained by an ordinary method according to formulations shown in Tables 2 to 5 below were all excellent in foaming, foam retention power, washing power and feeling upon use Incidentally, the amounts (values in the tables) of components shown in the tables are expressed by weight percent (%) when the amount of the whole composition is defined as 100.

TABLE 2

| Formulation Example 1 (Face wash foam) | (wt. %) |
| --- | --- |
| Sodium cocoyl glycinate | 18.0 |
| Hydroxypropyl starch phosphate | 2.0 |
| Glycerin | 38.0 |
| Cocamidopropyl betaine (30% solution) | 4.0 |
| Polyquaternium-39 (10% solution) | 1.0 |
| Lauric acid | 0.6 |
| Myristic acid | 1.2 |
| Stearic acid | 0.4 |
| Glycol distearate | 1.0 |
| Di(phytosteryl/octyldodecyl)lauroylglutamate | 0.2 |

TABLE 2-continued

| Formulation Example 1 (Face wash foam) | (wt. %) |
|---|---|
| Behenyl alcohol | 0.3 |
| Citric acid | 0.5 |
| Water | balance |
| | 100.0 |

TABLE 3

| Formulation Example 2 (Face wash powder) | (wt. %) |
|---|---|
| Sodium cocoyl glycinate | 15.0 |
| Sodium myristoylglutamate | 5.0 |
| Hydroxypropyl starch phosphate | 5.0 |
| Mannitol | 30.0 |
| Talc | 20.0 |
| Corn starch | 25.0 |
| | 100.0 |

TABLE 4

| Formulation Example 3 (Liquid face wash) | (wt. %) |
|---|---|
| Potassium cocoylglutamate (30% solution) | 20.0 |
| Hydroxypropyl starch phosphate | 1.5 |
| Cocoylalanine TEA (30% solution) | 20.0 |
| Myristic acid | 1.2 |
| Cocamide DEA | 2.0 |
| Butylene glycol | 3.0 |
| Glycerin | 2.0 |
| PEG-160 sorbitan triisostearate | 3.0 |
| Glycol distearate | 2.0 |
| Di(phytosteryl/octyldodecyl)lauroylglutamate | 0.2 |
| KOH | suitable amount |
| Citric acid | 0.5 |
| Water | balance |
| | 100.0 |

TABLE 5

| Formulation Example 4 (Face wash foam) | (wt. %) |
|---|---|
| Sodium lauroylglutamate | 35.0 |
| Hydroxypropyl starch phosphate | 2.0 |
| Myristic acid | 5.0 |
| Cocamide MEA | 1.0 |
| Butylene glycol | 10.0 |
| Dipropylene glycol | 20.0 |
| Talc | 1.0 |
| Di(phytosteryl/octyldodecyl)lauroylglutamate | 0.2 |
| KOH | suitable amount |
| Water | balance |
| | 100.0 |

Cosmetics excellent in washing power and foam properties and good in feeling upon use can be manufactured by mixing the N-long-chain-acyl amino acid and/or its salt, especially the N-long-chain-acyl neutral amino acid and/or its salt with hydroxypropyl starch phosphate.

The invention claimed is:

1. A composition comprising:
   (a) 3 to 50 wt % of an N-long-chain-acyl amino acid, a salt of an N-long-chain-acyl amino acid, or mixtures thereof, wherein the amino acid component of said N-long-chain-acyl amino acid is glycine and the acyl group of said N-long-chain-acyl amino acid is derived from a saturated or unsaturated fatty acid having from 8 to 22 carbon atoms; and
   (b) hydroxypropyl starch phosphat;
   wherein the weight ratio of said N-long-chain-acyl amino acid to said hydroxypropyl starch phosphate ranges from 99:1 to 70:30.

2. The composition according to claim 1, wherein said composition further comprises a fatty acid.

3. The composition according to claim 1, wherein said composition further comprises an acyl acidic amino acid ester.

4. The composition according to claim 3, wherein said acyl acidic amino acid ester is selected from the group consisting of di(cholesteryl/behenyl/octyldodecyl) N-lauroyl-L-glutamate, di(cholesteryl/octyldodecyl) N-lauroyl-L-glutamate, di(phytosteryl/octyldodecyl) N-lauroyl-L-glutamate, and di(phytosteryl/behenyl/octyldodecyl) N-lauroyl-L-glutamate.

5. The composition according to claim 4, wherein said acyl acidic amino acid ester is di(phytosteryl/behenyl/octyldodecyl) N-lauroyl-L-glutamate.

6. The composition according to claim 4, wherein said acyl acidic amino acid ester is di(phytosteryl/octyldodecyl) N-lauroyl-L-glutamate.

7. The composition according to claim 1, wherein the weight ratio of said N-long-chain-acyl amino acid to said hydroxypropyl starch phosphate is from 97:3 to 70:30.

8. The composition according to claim 2, wherein the weight ratio of said N-long-chain-acyl amino acid to said fatty acid is from 99:1 to 50:50.

9. The composition according to claim 3, wherein the weight ratio of said N-long-chain-acyl amino acid to said acyl acidic amino acid ester is from 99.9:0.1 to 70:30.

10. The composition according to claim 1, wherein said composition further comprises one or more additives selected from the group consisting of oils, surfactants, thickeners, antiseptics, aromas, ultraviolet absorbers, humectants, physiologically active ingredients, quasi-drugs, antioxidants, anti-inflammatory agents, antibacterial agents, antiperspirants, chelating agents, neutralizers, and pH adjustors.

11. The composition according to claim 1, wherein said composition is formulated as a consumer product selected from the group consisting of a cosmetic, a body wash, a facial wash, a shampoo, a hair-care product, a makeup remover, and a shaving cream.

12. A method of improving foaming properties comprising mixing from 3 to 50 wt % of an N-long-chain-acyl amino acid, a salt of an N-long-chain-acyl amino acid, or mixtures thereof, with hydroxypropyl starch phosphate to form a mixture, wherein the amino acid component of said N-long-chain-acyl amino acid is glycine and the acyl group of said N-long-chain-acyl amino acid is derived from a saturated or unsaturated fatty acid having from 8 to 22 carbon atoms, and further wherein the weight ratio of said N-long-chain-acyl amino acid to said hydroxypropyl starch phosphate ranges from 99:1 to 70:30.

13. The method of improving foaming properties according to claim 12, wherein said method further comprises improving washing power by admixing a fatty acid with said mixture.

14. The method of improving foaming properties according to claim 12, wherein said method further comprises improving removing properties of cosmetic compositions by admixing an acyl acidic amino acid ester with said mixture.

* * * * *

UNITED STATES PATENT AND TRADEMARK OFFICE
CERTIFICATE OF CORRECTION

PATENT NO. : 7,867,961 B2
APPLICATION NO. : 11/685421
DATED : January 11, 2011
INVENTOR(S) : Kazuhiko Tobita It is certified that error appears in the above-identified patent and that said Letters Patent is hereby corrected as shown below:

On the title page, Item (63), the Related U.S. Application Data information is incorrect. Item (63) should read:

-- Related U.S. Application Data

(63) Continuation of application No. PCT/JP2005/017101, filed on Sep. 9, 2005. --

Signed and Sealed this
Fifteenth Day of March, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,867,961 B2 | Page 1 of 1 |
| APPLICATION NO. | : 11/685421 | |
| DATED | : January 11, 2011 | |
| INVENTOR(S) | : Kazuhiko Tobita | |

It is certified that error appears in the above-identified patent and that said Letters Patent is hereby corrected as shown below:

Please change the following:

In column 8, line 4, "phosphat" should read --phosphate--.

Signed and Sealed this
Thirty-first Day of May, 2011

David J. Kappos
*Director of the United States Patent and Trademark Office*